United States Patent [19]

Powell et al.

[11] 4,116,565
[45] Sep. 26, 1978

[54] ELECTROPHORETIC ANALYZER WITH AUTOMATIC REFERENCE CIRCUIT

[75] Inventors: William E. Powell; Richard G. Magner, both of Raleigh, N.C.

[73] Assignee: Corning Glass Works, Corning, N.Y.

[21] Appl. No.: 799,944

[22] Filed: May 24, 1977

[51] Int. Cl.² .......................................... G01N 27/26
[52] U.S. Cl. ..................................... 356/105; 346/13; 346/33 A; 356/203
[58] Field of Search ................. 356/105, 203; 346/13, 346/33 A; 250/559

[56] References Cited

U.S. PATENT DOCUMENTS

| | | | |
|---|---|---|---|
| 3,479,265 | 11/1969 | Elevitch | 204/180 |
| 3,623,812 | 11/1971 | Hannig et al. | 356/105 |
| 3,635,808 | 6/1972 | Elevitch | 204/180 G |
| 3,706,877 | 12/1972 | Clifford, Jr. et al. | 346/13 X |
| 3,750,187 | 7/1973 | Keefer | 346/13 X |
| 3,902,813 | 9/1975 | VandenBroek et al. | 356/203 X |

FOREIGN PATENT DOCUMENTS 1,055,518  1/1967  United Kingdom ................... 346/13

OTHER PUBLICATIONS

Gelman Instrument Company, "ACD-15 Automatic Computing Densitometer," (Product Brochure).

Primary Examiner—John K. Corbin
Assistant Examiner—Matthew W. Koren
Attorney, Agent, or Firm—Walter S. Zebrowski; Clarence R. Patty, Jr.; Richard E. Kurtz

[57] ABSTRACT

An analyzer for electrophoretic samples has a sample stage movable linearly with respect to a source and a detector of analysis energy. During a first scan of the sample, a voltage is produced representing either the minimum detected fluorescence or the minimum detected optical density. During a second scan, the voltage is combined with the output of the detector to automatically correct the output to a reference.

9 Claims, 4 Drawing Figures

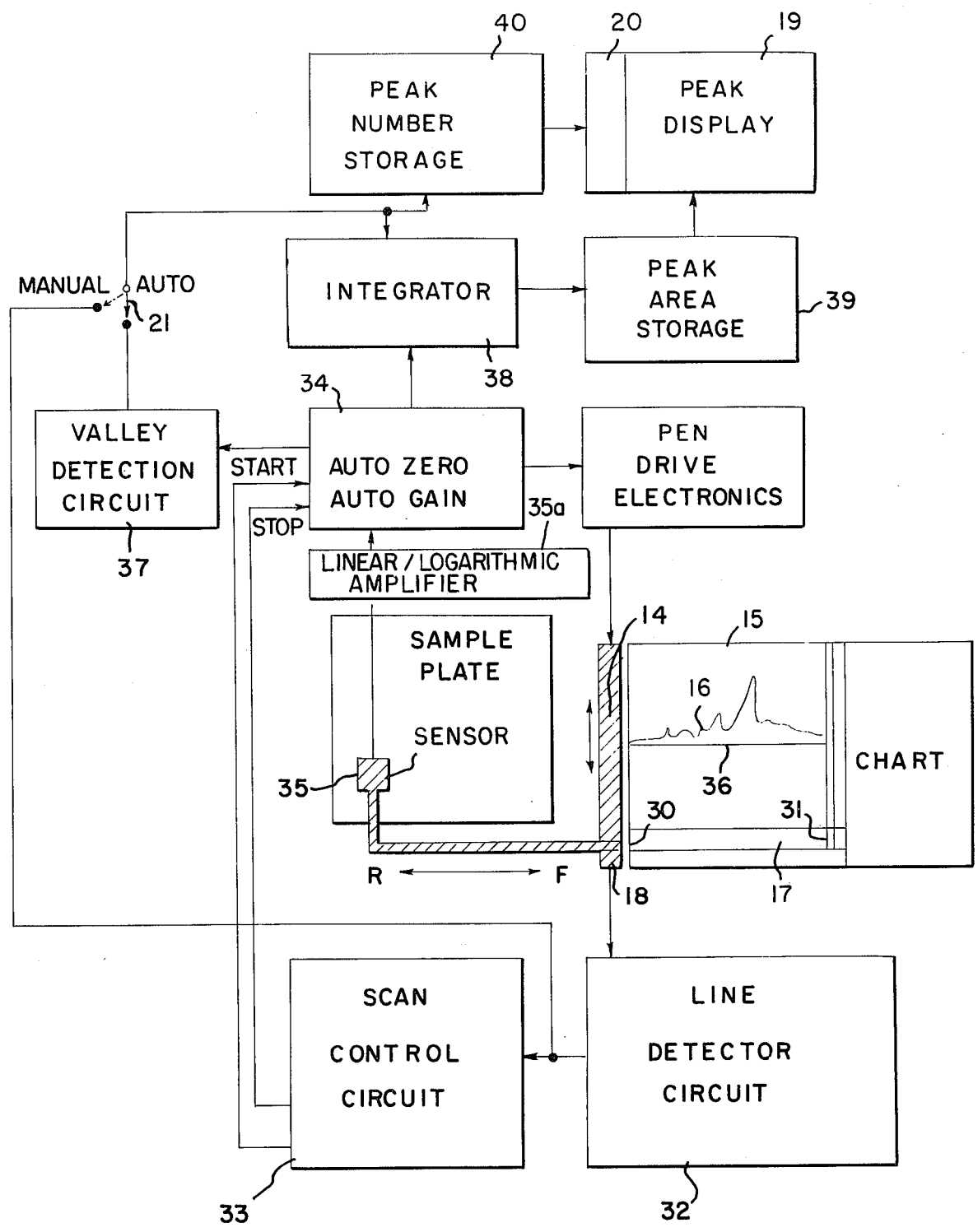

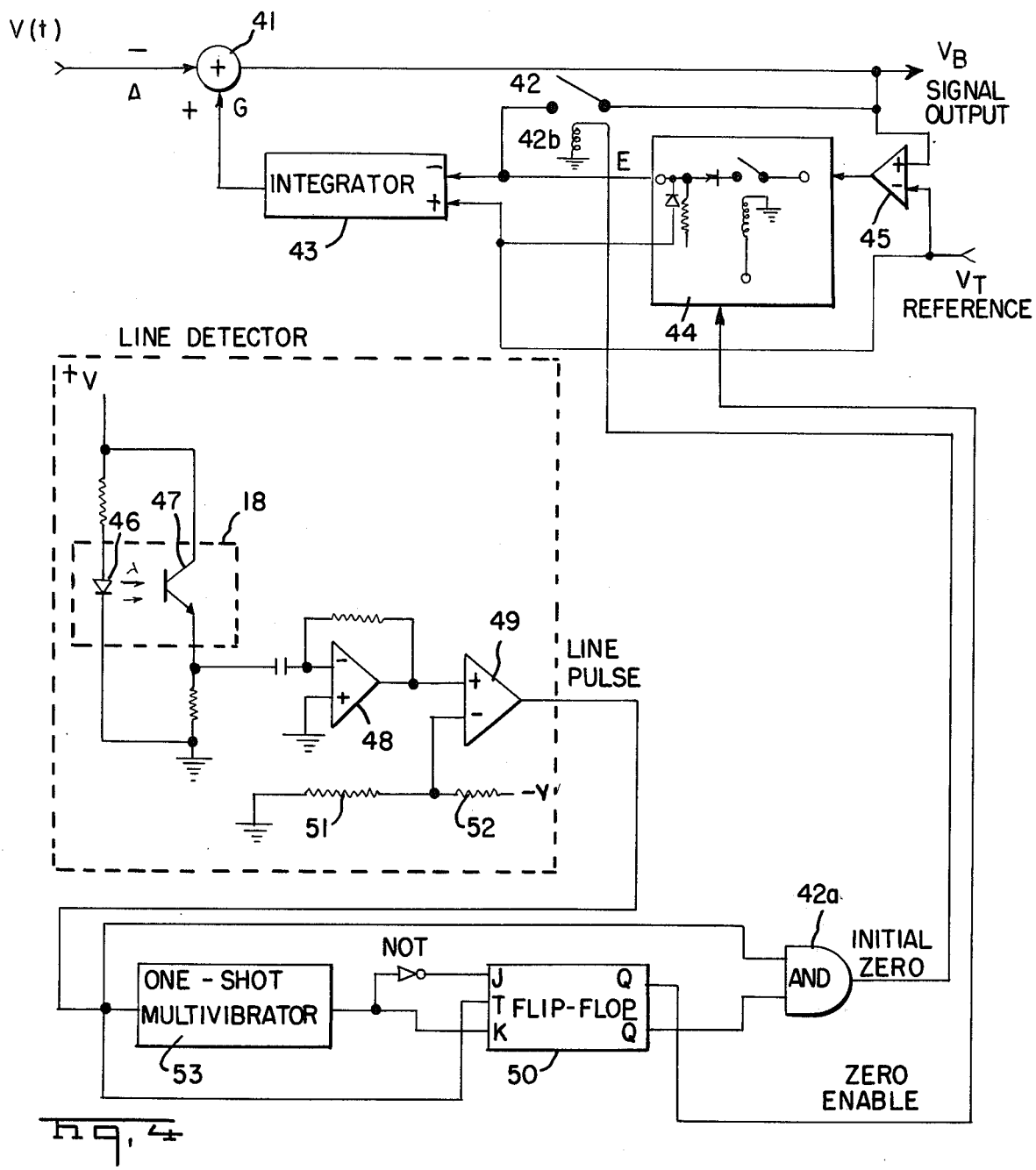
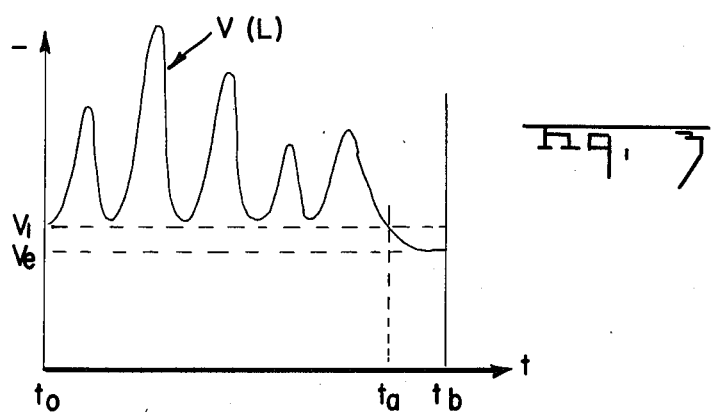

ELECTROPHORETIC ANALYZER WITH AUTOMATIC REFERENCE CIRCUIT

BACKGROUND OF THE INVENTION

This invention relates to an automatic recording fluorometer/densitometer, and more particularly to an automatic reference circuit for such an instrument.

A recording fluorometer/densitometer is used to analyze the optical characteristics of a sample such as a clinical electrophoresis plate.

U.S. Pat. Nos. 3,479,265 and 3,635,808 disclose thin film agarose sample plates which can be used as the electrophoretic medium. The thin film samples of these patents are particularly convenient for handling and storage.

These samples are analyzed by fluorometric or densitometric optical detection. One instrument for automatically making analyses of this type is described in U.S. Pat. No. 3,706,877. In such an instrument, the total area under the recorded analog curve is integrated, and this value is stored. Also, the area under selected peaks of the curve is determined by integration and this area is stored as a percent of the total area.

Integration, and other quantization of detected outputs such as this require that the output be referenced to a voltage which is usually zero. This voltage is called correction for zero offset. In such instruments, it is common to use the voltage output at the beginning of the scan as the zero offset correction voltage. However, it often happens that this does not produce a true zero because the voltage at the beginning of the scan may not be the true minimum in detector output during the scan.

RELATED APPLICATIONS

Application Ser. No. 800,004, filed May 24, 1977 shows the detection optics for the analyzer of the present invention, and application Ser. No. 799,942, filed May 24, 1977 shows the scan and recording mechanism of the analyzer of this invention. The disclosures of those applications are incorporated herein by reference.

DESCRIPTION OF THE DRAWINGS

FIG. 2 is an electrical block diagram of the system;
FIG. 3 shows a typical output of the detector of analysis energy;
FIG. 4 is a circuit diagram of the automatic referencing circuit of this invention together with the line detector and scan control circuitry.

DESCRIPTION OF THE PREFERRED EMBODIMENT

Figure 1:
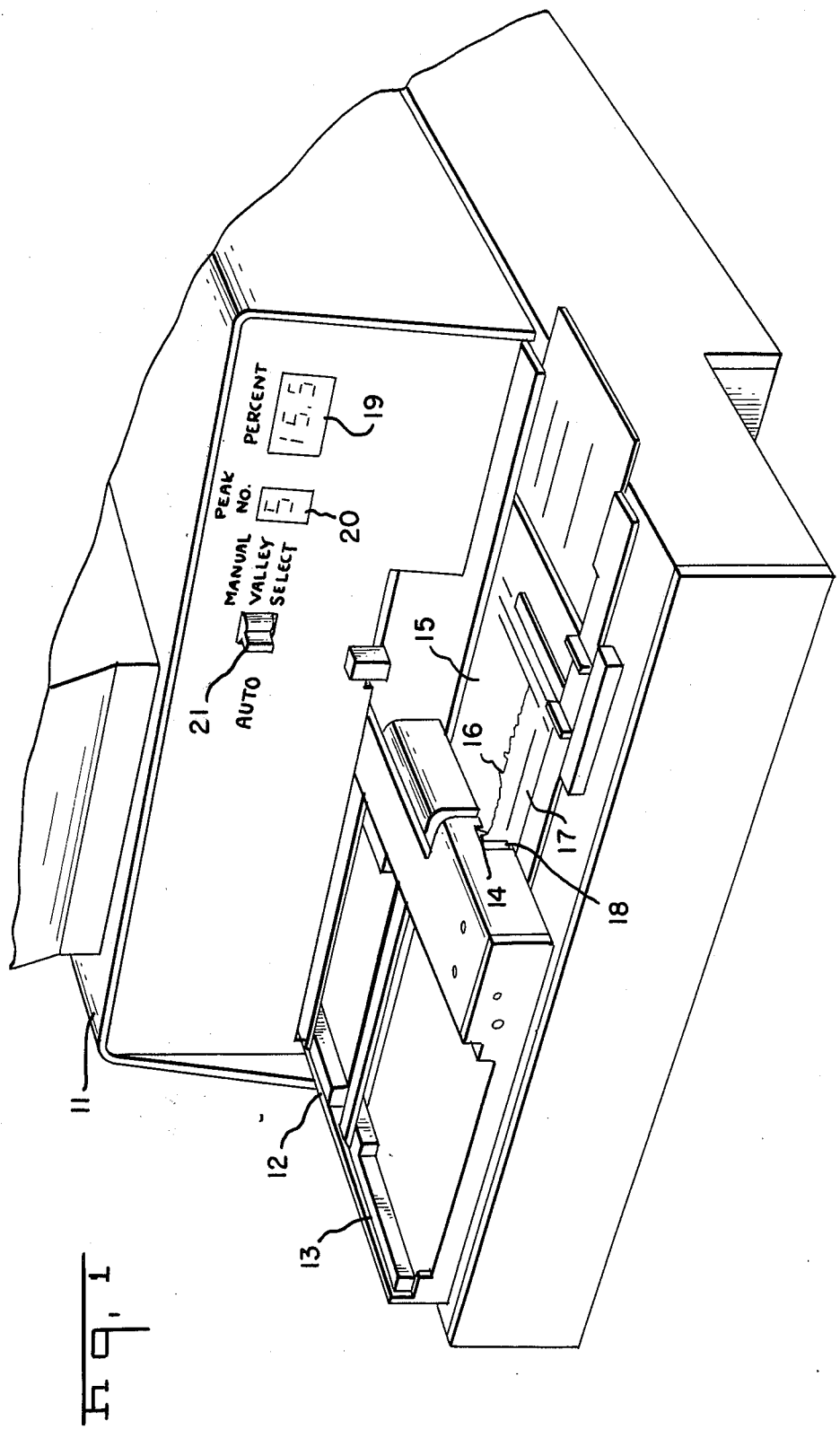
FIG. 1 shows the analyzer of this invention.

The instrument of this invention includes a case 11 which encloses fluorometric and densitometric sources of analysis energy and optics. For automatic recording, the film sample is inserted in the sample holder 12. The sample holder slides into the case between the light sources and the detector optics. The sample stage 13 moves in a horizontal direction to scan the analysis energy across the film. Concurrently, a recording pen 14 moves across the chart 15. A detector measures analysis energy intensity from the sample and a detector amplifier produces a signal representing the optical characteristics of the sample. A recording system responds to this signal to move the recording pen 14 orthogonally to the scanning motion. This records the intensity of fluorescence light emission or densitometric light absorption by the sample.

The pen 14 is moved along chart 15 by the same movement which scans the sample across the source. This produces a record 16 of fluorescence or optical absorption across the sample.

The chart 15 has a mark track 17. A line mark detector 18 is mounted on the stage 13. It is moved along the mark track 17 by the same movement which scans the sample and makes the record 16. A record is produced by a forward, left to right, scan and a return, right to left, scan. On the forward scan, automatic circuits are conditioned to store the minimum and the maximum of the detected signal, starting with the first line mark in track 17 which is detected by line detector 18. This continues until the line detector 18 detects a double line mark at the right hand end of the track 17. These marks define the scan width. On the return scan, the record 16 is drawn on the chart 15 and integration limits (valleys) are automatically selected for each peak. An integrator integrates the area of each peak under the record 16. The area of each peak as the percentage of the total area of all peaks is determined. These percentages are displayed on digital display 19. Digital display 20 displays the number of the peak.

If the operator finds that the automatic valley marks are not suitable because they are misplaced, missing, or more than needed are marked, the operator may select more suitable valleys by adding valley marks to the mark track 17 of the card. A pencil will make suitable marks. The switch 21 is turned from the automatic position to the "Manual Valley Select" position. A second scan forward by scanning stage 13 while in the manual mode is used to count the marks (valleys and scan window). On the return scan, a second integration is performed using the manual valley marks. The percentage area and number of each peak as defined by the manually inserted marks is then displayed on displays 19 and 20.

FIG. 2 shows an electrical block diagram of the analyzer. On the forward scan, line mark detector 18 detects the mark 30 and the double mark 31. These define the width of the scan. Line mark detector circuit 32 converts the output of the mark detector phototransistor to pulses which are converted to start and stop pulses by the scan control circuit 33. Start and stop pulses enable circuits 34 which store the maximum and minimum signal output of the linear/logarithmic amplifier 35a during the forward scan. The amplifier 35a includes a logarithmic amplifier for use in the densitometric mode, and a linear amplifier for the fluorometric mode. The recorder 14 draws a base line 36 on this forward scan. At the end of the forward scan, the minimum output of detector 35 is used to determine the data level zero and the maximum output is used to set the gain of the amplifier in circuit 34 so that the pen of recorder 14 always has a fixed displacement from zero for this signal.

On the return scan, the valley detection circuit 37 automatically selects valleys before, after, and between data peaks. An integrator 38 is enabled during the intervals between the valleys. The outputs of the integrator are stored and displayed as a percentage of the total area of all peaks. While different types of integrators are suitable for use, one particularly suitable for use includes a digital pulse counter. A voltage to frequency converter converts the output of circuit 34 into a pulse train, the frequency of which is proportional to the amplitude of the record 15. These pulses are counted between valley points. The counts between valley points are divided by the total count to obtain an expression of the area of each peak as a percentage of the total area. These percentages are stored in storage 39, and the number of the corresponding peak is stored in storage 40. These are then displayed on the digital displays 19 and 20.

If the operator is not satisfied with the automatically selected valley points, he manually inserts valley marks on the track 17. Switch 21 is turned from the position shown to the manual position. In this mode, pulses from the line mark detector circuit 32 determine the valley points between which integrator 38 counts pulses.

In order to correctly integrate the area under the various peaks, it is necessary to accurately and repeatedly correct the minimum detector output during a scan to a reference, which is usually zero.

FIG. 3 depicts a typical detector signal during a scan which produced five peaks. Assuming that the scan starts at the left, in accordance with prior art practice the voltage $V_1$ would be selected as the zero offset voltage, and this voltage would be subtracted from the detector output to provide a reference for the output. However, this is not necessarily the correct reference. As shown in FIG. 3, the correct reference is $V_e$ which occurs at the end of the scan. In practice, a minimum can occur any place in the scan.

FIG. 4 shows the amplifier auto zero circuit 34 which produces a zero offset voltage corresponding with the minimum detector signal during the first scan, and applies this voltage as a zero offset during a second scan. The output of the linear/logarithmic amplifier 35a, $V(t)$, is applied to the A input of the signal summer 41. The signal summer 41 converts the output of the detector, which is negative going, into a positive going signal. At the beginning of the first scan, switch 42 is momentarily closed to apply the output $V_B$ of summer 41 to the integrator 43. This causes the output of the integrator to change until output $V_B$ is zero. Then a second switch 44 is closed. Comparator 45 compares the signal $V_B$ with a reference voltage $V_T$ which is assumed to be zero.

Switch 44 includes a unidirectional diode and an electrically controlled switch which, when closed, completes a path between comparator 45 and integrator 43. If the signal output $V_B$ is greater than or equal to zero, the output of switch 44 will be zero and the output of integrator 43 remains constant.

If the signal output $V_B$ goes negative (less than $V_T$), the output of switch 44 will be a negative voltage. This negative voltage is applied to inverting integrator 43 which causes the voltage at G to become more positive. As $V_G$ increases positively, the signal output $V_B = V_G - V_A$ becomes more positive. when $V_G - V_A$ again reaches zero, the comparator 45 will switch causing the voltage at E to become zero and the output of the integrator to remain constant.

The comparator 45 may switch many times during the first scan. This insures that the analog signal output $V_B$ will be referenced to zero ($V_T$). At the end of the first scan, the integrator has stored the voltage $V_E$. At this time, the switch 44 is turned off.

During the second scan, the linear/logarithmic amplifier produces a signal $V(t)$ which is applied to the A input of summer 41. (In the actual embodiment being described, the detector output will be reversed because the first scan is in the forward direction and the second scan is in the reverse direction.) During the second scan, the signal $V(t)$ is combined with the zero offset voltage $V_E$ in the summer 41. This produces a signal output $V_B$ which is correctly referenced to zero.

Thus far, we have assumed that the reference voltage $V_T$ is zero, but it will be appreciated that this can be any reference voltage.

The remaining circuitry in FIG. 4 is the line detector and scan control circuitry which controls the closures of switches 42 and 44. The line mark detector 18 includes a light emitting diode 46 and a phototransistor 47. When a line mark passes under the line mark detector 47, the phototransistor 47 produces an output which is applied to differentiating amplifier 48. Differentiating amplifier 48 produces a signal having a near-zero voltage at the time when phototransistor 47 reaches the maximum response to a detected line mark. The output of amplifier 48 is applied to a comparator 49 which switches when that output equals a reference voltage corresponding approximately to the point of maximum slope, set by resistors 51 and 52 thus locating the center of the mark. The effect of pulses from amplifier 49 is controlled as follows. Flip-flop 50 is presumed to be initially reset. The logic high at the $\overline{Q}$ output of 50 enables AND gate 42a. The initial pulse from amplifier 49 passes through gate 42a and energizes winding 42b which closes switch 42. The end of the first pulse from amplifier 49 de-energizes winding 42b, triggers one-shot 53, and sets flip-flop 50. The logic high at the Q output of flip-flop 50 activates switch 44 and the logic low at the $\overline{Q}$ output disables AND gate 42a. Subsequent pulses from amplifier 49 have no further effect unless they are separated by a time interval less than the pulse length of one-shot 53. One-shot 53 and flip-flop 50 serve to detect the double line marking the end of the first scan. The first input pulse from the double line triggers one-shot 53. The resulting high output of 53 inverts the logic levels at the J and K inputs of flip-flop 50. The second line pulse occurs while the output of one-shot 53 is still high and causes flip-flop 50 to reset. This inactivates switch 44.

While a particular embodiment of the invention has been shown and described, various modifications are within the true spirit and scope of the invention. The appended claims are intended to cover all such modifications.

What is claimed is:

1. An analyzer for electrophoretic samples comprising:
    a source of analysis energy,
    a detector producing a signal representing the optical characteristics of the sample,
    a sample stage movable linearly with respect to said source and said detector to scan a sample,
    means for generating a voltage representing the minimum in said signal during a first scan of said sample stage, and
    means for combining said voltage with said signal during a second scan of the said sample stage to automatically correct said signal to a reference.

2. The analyzer recited in claim 1 wherein said means for generating includes an integrator, the signal produced by said detector being applied to said integrator to generate said voltage during said first scan.

3. The analyzer recited in claim 2 wherein said means for combining includes a summer, the output of said integrator and the signal produced by said detector being applied to said summer during said second scan to automatically correct the signal produced by said detector to said reference during said second scan.

4. The analyzer recited in claim 3 further comprising:
a comparator, the output of said summer and a reference voltage being applied to said comparator, the output of said comparator being applied to said integrator only when the output of said summer exceeds said reference.

5. The analyzer recited in claim 4 further comprising first and second switch means, said first switch means being connected to momentarily apply the output of said summer to said integrator at the beginning of said first scan, said second switch means being connected to apply the output of said comparator to said integrator during the remainder of said first scan.

6. The analyzer recited in claim 5 further comprising a unidirectional conducting element in said second switch means.

7. The analyzer recited in claim 5 further comprising:
a line sensor mounted on said sample stage for detecting the beginning and end of a scan, said sensor being connected to actuate said first and second switch means.

8. The analyzer recited in claim 1 wherein said sample stage is movable linearly in a first direction during said first scan, and is movable linearly during said second scan.

9. The analyzer recited in claim 8 further comprising:
a recorder mounted on said sample stage, said recorder being operative during said first scan to produce a base line and being operative during said second scan to produce a record of the detected analysis energy.

* * * * *